United States Patent
Mouriño et al.

[11] Patent Number: 5,929,056
[45] Date of Patent: Jul. 27, 1999

[54] VITAMIN D COMPOUNDS AND METHOD OF PREPARING THESE COMPOUNDS

[75] Inventors: Antonio Mouriño; Jose Antonio Martinez; Maria de los Angeles Rey; Juan Granja, all of Santiago de Compostela, Spain; Sebastianus J. Halkes, Weesp, Netherlands

[73] Assignee: Duphar International Research B.V., Weesp, Netherlands

[21] Appl. No.: 08/570,560

[22] Filed: Dec. 11, 1995

[30]  Foreign Application Priority Data

Dec. 14, 1994 [EP]  European Pat. Off. ............ 94203616

[51] Int. Cl.⁶ .......................... A61K 31/59; C07C 401/00
[52] U.S. Cl. ............................. 514/167; 552/653
[58] Field of Search ............... 552/653; 517/167

[56]  References Cited

U.S. PATENT DOCUMENTS 5,545,633  8/1996  Bretting ................................. 514/167

FOREIGN PATENT DOCUMENTS

| 0387077 | 3/1990 | European Pat. Off. . |
| 0521550 | 6/1992 | European Pat. Off. . |
| 92/21695 | 12/1992 | WIPO . |
| 9401398 | 1/1994 | WIPO ........................ C07C 401/00 |

*Primary Examiner*—Jose' G. Dees
*Assistant Examiner*—Alton Pryor
*Attorney, Agent, or Firm*—Watson Cole Stevens Davis, P.L.L.C.

[57]  ABSTRACT

The present invention relates to vitamin D compounds of the general formula

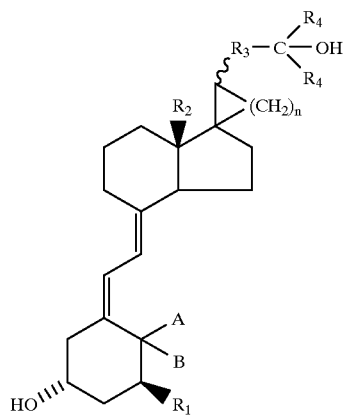

wherein:
  $R_1$ is a hydrogen atom or a hydroxy group;
  $R_2$ is a ($C_1$–$C_3$)alkyl group, a hydroxy($C_1$–$C_3$)alkyl group, a ($C_1$–$C_2$)alkoxymethyl group or a ($C_2$–$C_3$) alkenyl or alkynyl group;
  n is 1;
  $R_3$ is a branched or non-branched, saturated or unsaturated, substituted or unsubstituted aliphatic ($C_3$–$C_7$)hydrocarbon or oxyhydrocarbon biradical;
  $R_4$ is a branched or straight ($C_1$–$C_6$) alkyl group or a ($C_3$–$C_6$)cycloalkyl group; and
  A and B are each individually hydrogen atoms or methyl groups, or
  A and B form together a methylene group.

The present compounds find use in cosmetic application and in human and veterinary pharmacotherapeutic practice in the treatment of skin and bone diseases, diseases related to cell differentiation/cell proliferation, imbalance in the immune system and inflammatory diseases.

8 Claims, 6 Drawing Sheets

Reaction Scheme A
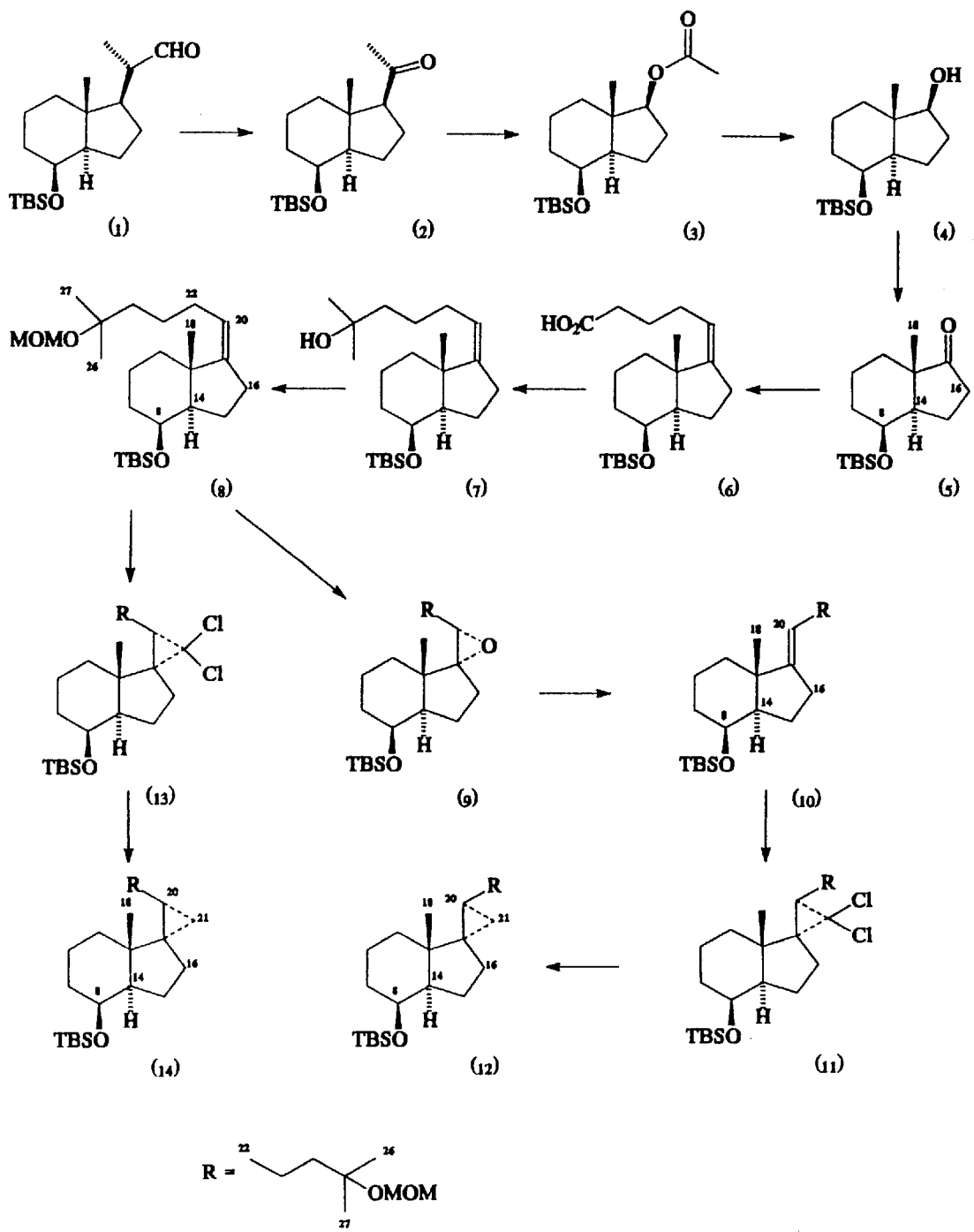

Reaction Scheme B
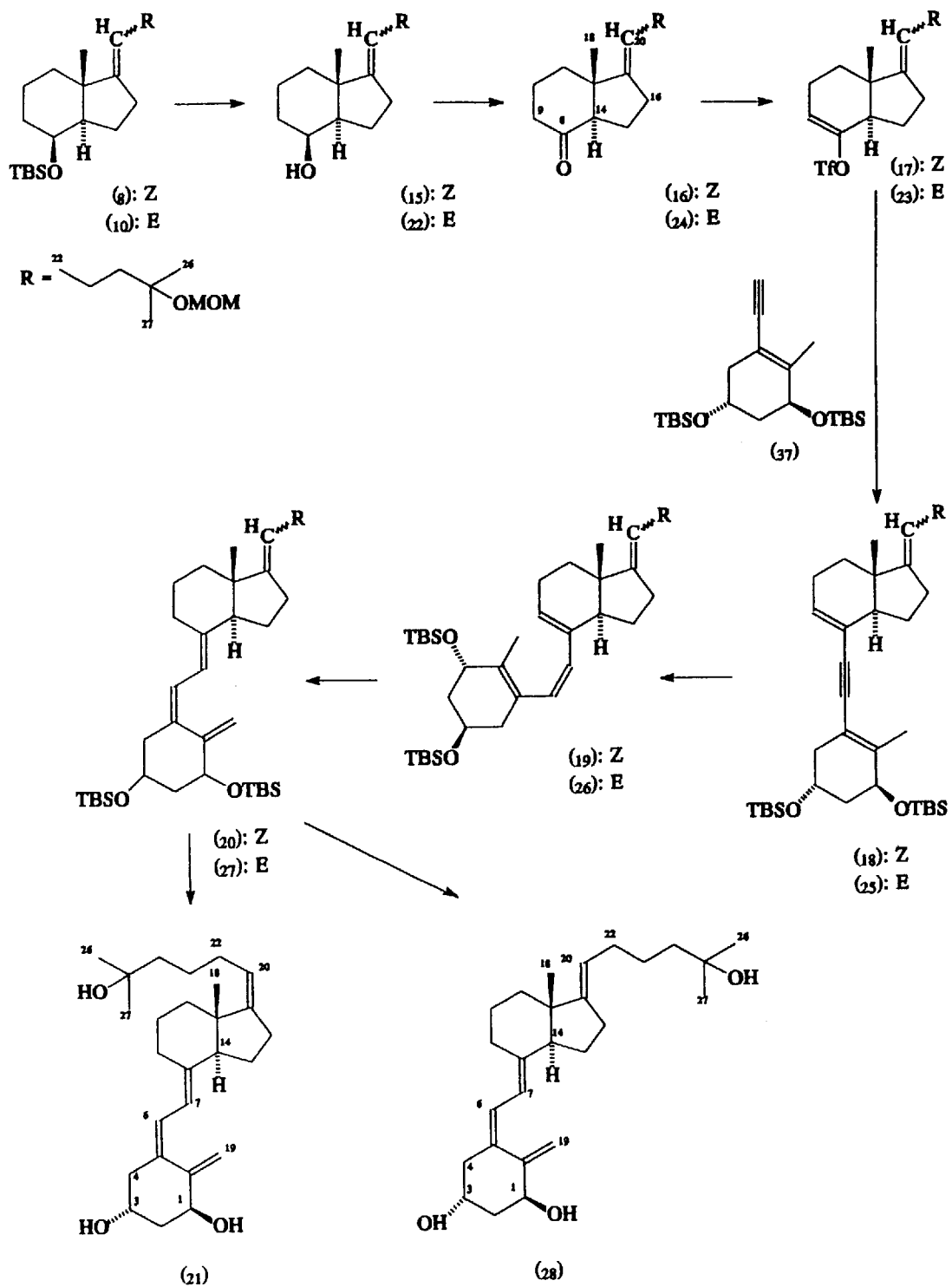

Reaction Scheme C
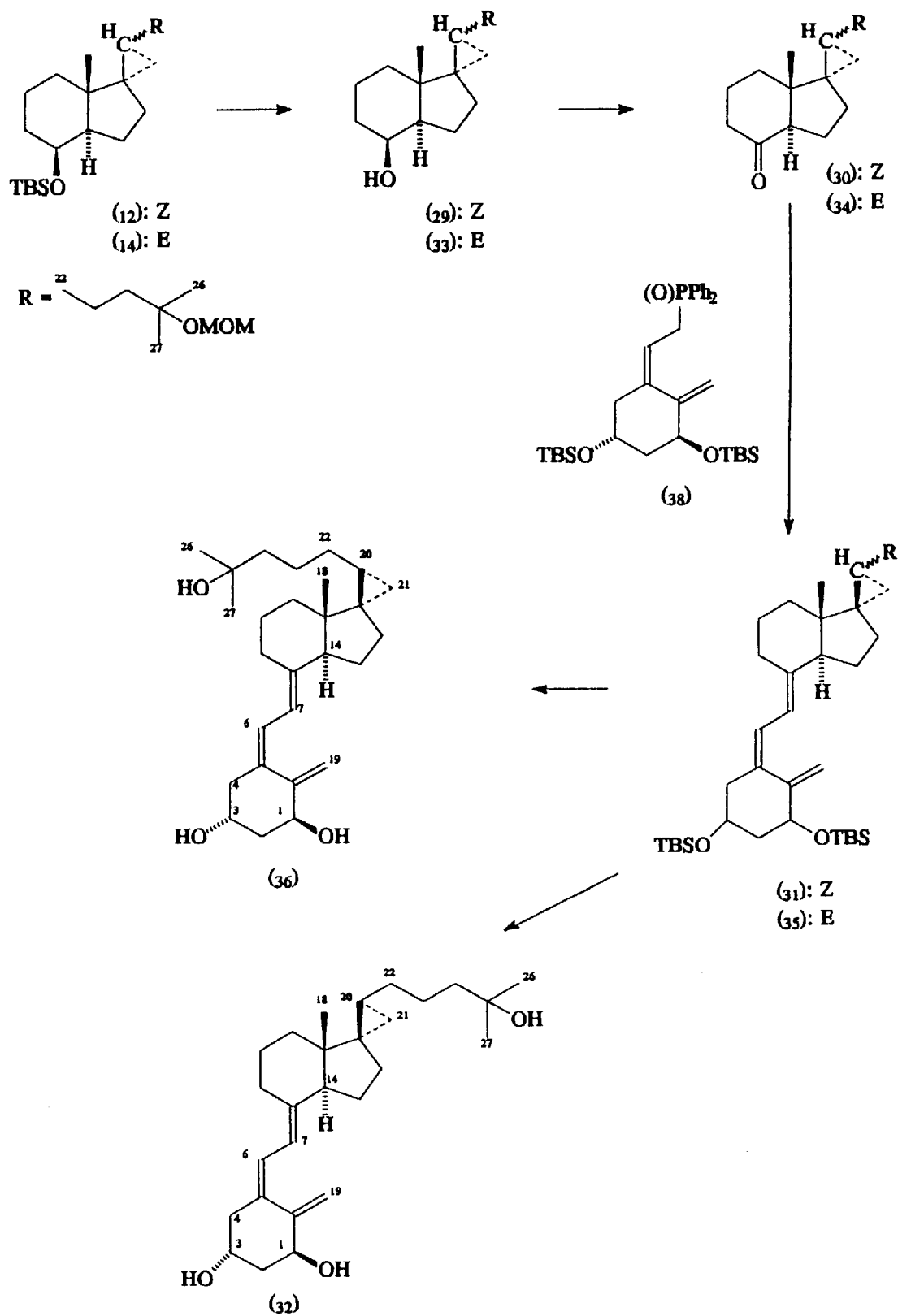

VITAMIN D COMPOUNDS AND METHOD OF PREPARING THESE COMPOUNDS

The invention relates to new vitamin D compounds, to a method of preparing these compounds and to their use in pharmacology. The invention further relates to valuable new intermediates.

It is generally known, that vitamin D compounds or vitamin D related compounds ("vitamin D compounds") have a strong biological activity and may be used in all those cases in which problems with the calcium metabolism play a part. A few years ago it was found that various active vitamin D compounds also have other pharmacotherapeutic activities and may be used successfully, for example, for the treatment of certain skin and bone diseases, for cosmetic applications and for treating diseases which are related to cell differentiation, cell proliferation or imbalance in the immune system, including diabetes mellitus, hypertension and inflammatory diseases such as rheumatoid arthritis and asthma. In addition, these compounds may be used in various veterinary applications, and for diagnostic purposes.

It is therefore of the utmost importance to have the disposal of an arsenal of active vitamin D compounds for the above various application fields so as to be able to make the best possible choice of a vitamin D compound for the application in view.

Vitamin D compounds which are of interest for the above applications are hydroxylated vitamin D compounds, in particular vitamin D compounds hydroxylated in the 1α-, 24- and/or 25-positions. Recent developments in the field of active vitamin D compounds are 19-nor-vitamin D compound (EP-A-0387077), 25,25-di(cyclo)alkyl vitamin D compounds (non-prepublished U.S. patent application 08/070,998) and (C-18)-modified vitamin D compounds (EP-A-0521550), preferably also hydroxylated in the 1α-position and optionally in the (C-17)-side chain. Other modifications of the (C-17)-side chain have been proposed, likewise to improve the intended activity and to suppress detrimental side-effects. Examples of modifications of the (C-17)-side chain are chain elongations (homo compounds), 22-oxa modifications, fluor substitutions, epoxy groups (e.g. WO 92/21695), etc. Generally, however, the above (C-17)-side chain modified vitamin D compounds are still not completely satisfactory as regards their selective activity, i.e. the intended activity without detrimental side-effects.

Further, the accessibility of the (C-17)-side chain modified vitamin D compounds is often insufficient or unattractive. In this connection there is a need for better accessible (C-17)-side chain modified vitamin D compounds. As a matter of fact, both the starting compounds for the preparation of such vitamin-D compounds must be easily available or accessible, and the multistep preparation process must lead to the intended purpose with sufficient selectivity and efficiency.

It is therefore the objective of the present invention to provide a new class of vitamin D compounds, which is well accessible from readily available or accessible starting materials.

According to the present invention this objective can be achieved with a new vitamin D compound of the general formula

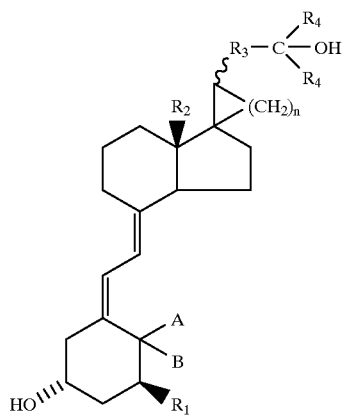

(I)

wherein:

$R_1$ is a hydrogen atom or a hydroxy group;

$R_2$ is a $(C_1-C_3)$alkyl group, a hydroxy$(C_1-C_3)$alkyl group, a $(C_1-C_2)$alkoxymethyl group or a $(C_2-C_3)$ alkenyl or alkynyl group;

n is 0 or 1;

$R_3$ is a branched or non-branched, saturated or unsaturated aliphatic $(C_3-C_7)$hydrocarbon or oxahydrocarbon biradical, having at least 3 atoms in the main chain and being optionally substituted with one or more substituents selected from fluoro, hydroxy, epoxy or methoxy;

$R_4$ is a branched or straight $(C_1-C_6)$alkyl group or a $(C_3-C_6)$cycloalkyl group; and A and B are each individually hydrogen atoms or methyl groups, or A and B form together a methylene group.

The above new (C-17)–(C-20)-modified vitamin D compounds of the invention, presented by the general formula I, are valuable substances. The biological results indicate that these compounds are promising as biologically active substances and may be used in all above-mentioned pharmacotherapeutic indications, more in particular for the treatment of osteoporosis, renal osteodystrophy, osteomalacia, skin disorders such as psoriasis (and other hyperproliferative skin diseases), eczema and dermatitis, myopathy, leukaemia, breast and colon cancer, osteosarcomas, squamous cell carcinomas, melanoma, certain immological disorders, and transplant rejections. For this application, the new compounds of the invention may be incorporated, in effective amounts, in pharmaceutical compositions, comprising in addition pharmaceutical acceptable carriers and auxiliary substances.

Furthermore, the new vitamin D compounds of the invention may be used for wound healing and may be incorporated in cosmetic compositions, such as creams, lotions, ointments and the like, in order to preserve, condition and/or protect the skin and to improve various skin conditions, such as wrinkles, dry skin, skin slackness and insufficient sebum secretion. The new vitamin D compounds may also be used for diagnostic purposes.

Preferred is a vitamin D compound of the general formula (II)

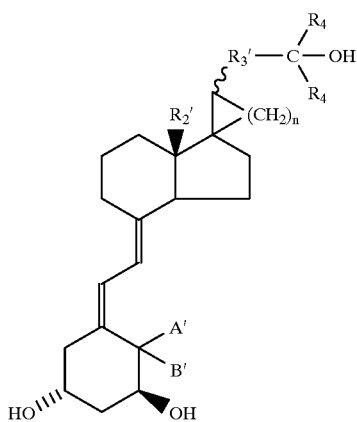

wherein:
R$_4$ and n have the above meanings;
R$_2$' is CH$_3$, CH$_2$CH$_3$, CH$_2$OH or CH=CH$_2$;
R$_3$' is a biradical of the formula

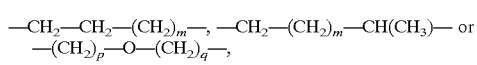

wherein m=0–3; p=0–3 and q=1–3, with the proviso that p+q=≧2; and
A' and B' are hydrogen atoms or form together a methylene group.

In the above formula II compounds R$_4$ means preferably methyl, ethyl, propyl, isopropyl or cyclopropyl, and R$_2$' is preferably methyl.

It is a merit of the present invention, that the desired C-20 stereoisomers can easily be obtained, as will be explained hereinafter. Therefore the present invention also relates to a vitamin D compound as defined hereinbefore, wherein the (C-20) substituent, i.e. the substituent R$_3$—C(R$_4$)$_2$—OH in formula I, has either the E or the Z configuration.

The invention also relates to a method of preparing a vitamin D compound of the above formula I as defined above, by subjecting a hydrindane compound of the general formula (IV)

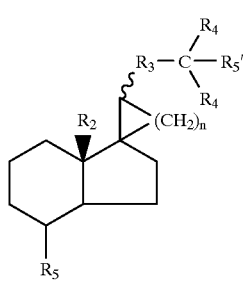

wherein:
R$_2$, R$_3$, R$_4$, and n have the above meanings; and
R$_5$ and R$_5$' are protected hydroxy groups;
to deprotection of substituent R$_5$ and then to an oxidation to the corresponding hydrindane-4-one compound of the general formula (V)

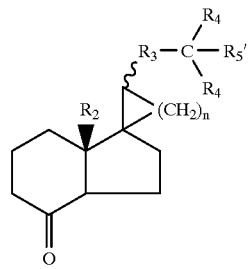

which compound of formula V is then converted either
(a) with a Wittig reagent of the general formula (VI)

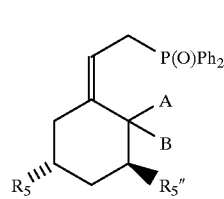

wherein:
R$_5$, A and B have the above meanings; and
R$_5$" is a hydrogen atom or a protected hydroxy group;
or (b), after enolization and derivatization of the enolic hydroxy group, with an enyne compound of the general formula (VII)

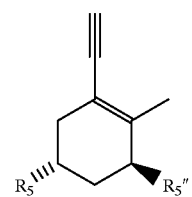

wherein R$_5$ and R$_6$" have the above meanings, followed by partial hydrogenation and isomerization, to produce a compound of the general formula I, wherein A and B form together a methylene group; followed by deprotection.

Hydroxy groups in the above intermediates or reactants may be protected by a reaction with a suitable esterification or etherification agent. A suitable esterification agent is an alkylchlorocarbonate having 2 to 5 carbon atoms, or an aromatic carboxylic acid or saturated aliphatic carboxylic acid having 1 to 4 carbon atoms such as benzoic acid, or a derivative of such acids suitable for the esterification reaction. In order to protect in the form of an ether, in principle any etherification agent known for this purpose is suitable: for example, a methoxymethylating agent (such as methoxymethylchloride), a trialkylsilylimidazole, a trialkylsilylhalide, a trialkyl-silyltriflate (-trifluoromethanesulfonate), a diphenylalkylsilylhalide, or a diphenylalkylsilyltriflate, or a derivative thereof, the alkyl groups of which have 1 to 6 carbon atoms. Particularly suitable for this purpose are trimethylsilylchloride, tert.-butyldimethylsilylchloride, dimethyl-(1,1,2-trimethylpropyl)-silylchloride, tert.-butyldimethylsilyl triflate, or trimethylsilyl-imidazole, because these etherification agents readily react with the hydroxy group to be protected to form an ether function, which on the one hand is sufficiently stable under the conditions of the reaction or reactions in view, but on the other hand can easily be removed [deprotection] to recover the original hydroxy group; tert.-butyldimethylsilylchloride or triflate is to be preferred, because the tert.-butyldimethylsilyl group has been found to be excellently suitable as a protective group.

The enolic hydroxy group is preferably derivatized by a reaction with N-phenyltriflimide to produce a triflate.

As indicated above, the desired C-20 stereoisomers are readily accessible in a high stereochemical purity. Therefore the present invention relates also to the synthesis of a specific (C-20)-stereoisomeric vitamin D compound of the general formula

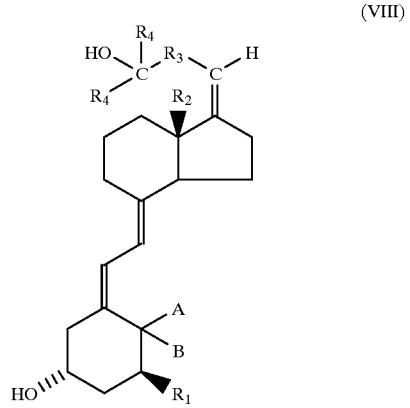
(VIII)

wherein the symbols have the meanings given hereinbefore; by reacting a compound of the general formula

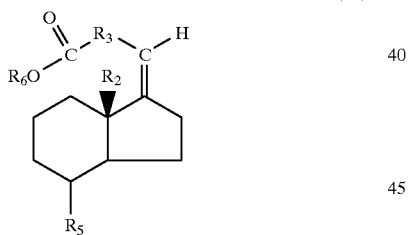
(IX)

wherein:
$R_2$ and $R_3$ have the above meanings,
$R_5$ is a protected hydroxy group, and
$R_6$ is a hydrogen atom or a $(C_1-C_6)$alkyl group;
with an organometallic compound of the general formula

$R_4M(X)_p$ wherein:
$R_4$ has the above meaning,
X is Cl, Br or I,
M is a metal selected from Li and Mg, and
p is, dependent on the valence of M, 0 or 1;
after which the hydrindane compound obtained, after protection of the free hydroxy group, has the general formula

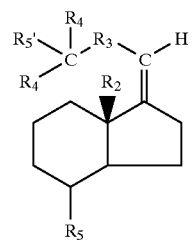
(X)

which compound of formula X is selectively deprotected, and then oxidized to the corresponding hydrindane-4-one compound of the general formula

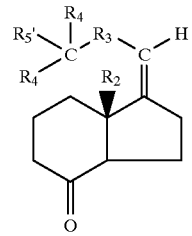
(XI)

which compound of formula XI, if desired after protection of the hydroxy group, is then converted either
(a) with a Wittig reagent of the general formula

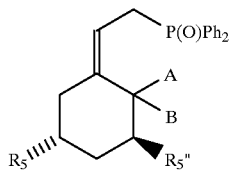
(VI)

wherein $R_5$, $R_5''$, A and B have the above meanings;
or (b), after enolization and derivatization of the enolic hydroxy group, with an enyne compound of the general formula

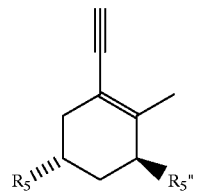
(VII)

wherein $R_5$ and $R_5''$ have the above meanings, followed by hydrogenation and isomerization, to produce a compound of the general formula I, wherein A and B form together a methylene group; followed by deprotection.

Suitable examples of organometallic compounds are compounds of the formula

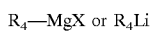
$R_4$—MgX or $R_4$Li wherein $R_4$ has the meaning given above and X is a halogen atom. Examples of suitable reagents for the above reaction are: $R_4$—MgBr, $R_4$—MgI, $R_4$—MgCl and $R_4$—Li, wherein $R_4$ is defined above.

Alternatively compounds of the general formula VIII as defined above can be prepared by reacting a compound of the general formula

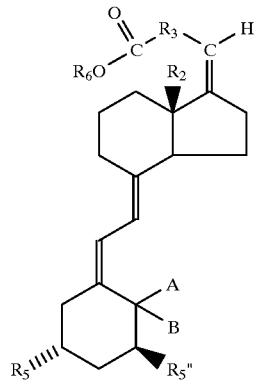 (XIX)

wherein:

$R_2$, $R_3$, $R_5$, $R_5''$, A and B have the above meanings; with an organometallic compound of the general formula $$R_4M(X)_p$$

wherein:

$R_4$, M, X and p have the meanings given above; followed by deprotection.

The other (C-20)stereoisomers can also be synthesized, e.g. starting from the above-defined hydrindane compound X. So a vitamin D compound of the general formula

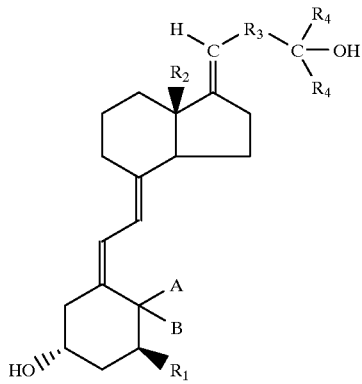 (XII)

wherein the symbols have the meanings given in above;

is prepared by subjecting the hydrindane compound of the general formula X, defined hereinbefore, to an epoxidation of the C—C double bond, producing a compound with the general formula

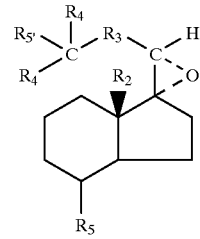 (XX)

followed by removal of the epoxide-oxygen, producing a hydrindane compound of the general formula

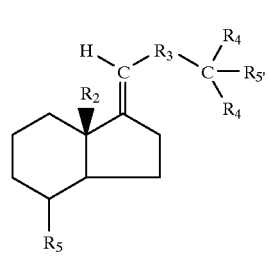 (XIII)

followed by the successive reaction steps as defined above.

A vitamin D compound of the general formula

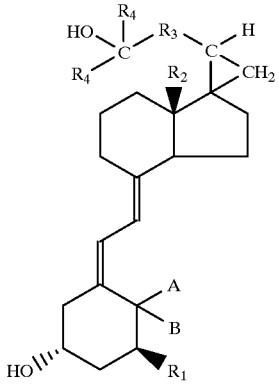 (XIV)

wherein the symbols have the meanings given hereinbefore; can readily be prepared by subjecting the hydrindane compound of the general formula X, defined hereinbefore, successively to an addition of dichlorocarbene to the C—C double bond (formula XXI, Z configuration) and to a reduction, producing a hydrindane compound of the general formula XV,

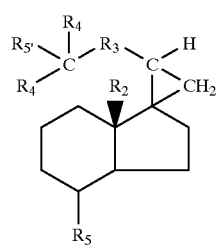 (XV)

(XXI)

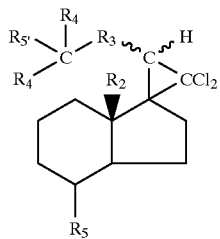

followed by the successive reaction steps as defined above.

Finally, a vitamin D compound of the general formula (XVI)

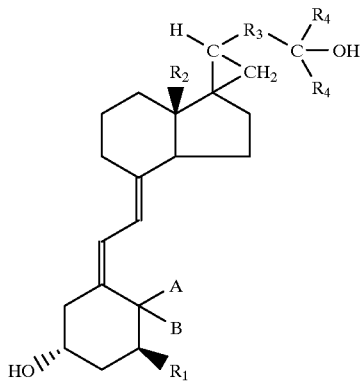

wherein the symbols have the meanings given hereinbefore; is prepared by subjecting the hydrindane compound of the general formula XIII, defined hereinbefore, successively to an addition of dichlorocarbene to the C—C double bond (formula XXI, E configuration) and to a reduction, producing a hydrindane compound of the general formula XVII, (XVII)

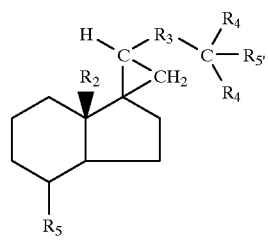

(XXI)

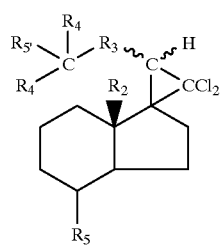

followed by the successive reaction steps as defined above.

The starting ester compound of formula IX can conveniently be prepared from a readily available substance, viz. vitamin $D_2$, as follows:

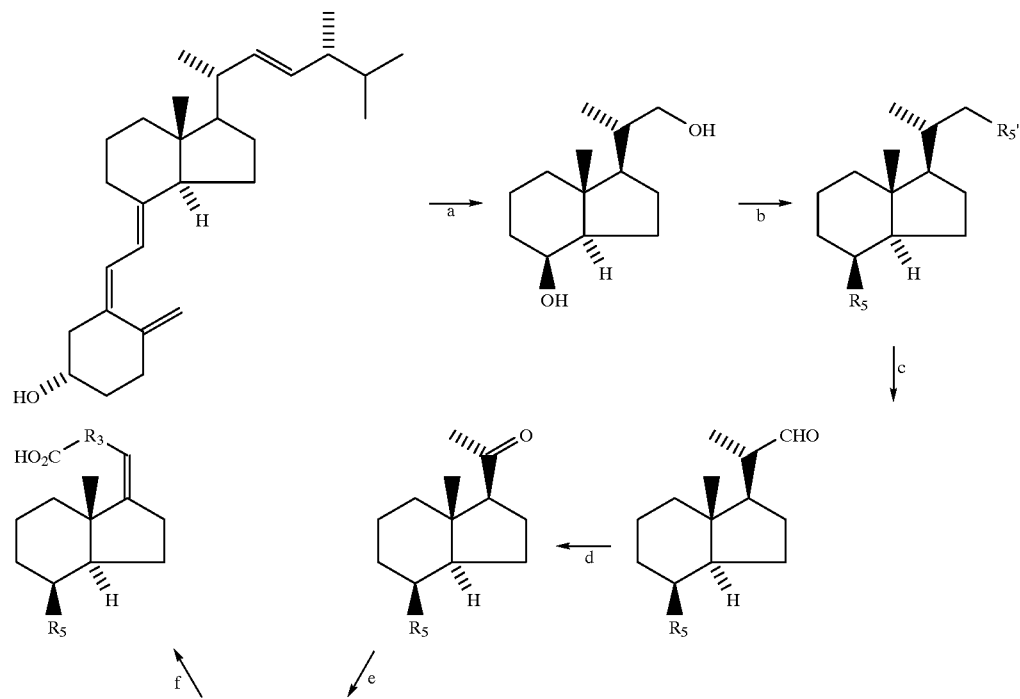

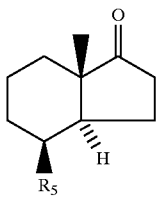

Vitamin $D_2$ is degraded (reaction step a), e.g. by an ozonolysis-reduction reaction, to the so-called Inhoffen-Lythgoe diol, which, after protection (reaction step b), is oxidized (reaction step c) to yield an aldehyde. This aldehyde is subjected to an oxidative degradation (reaction step d), after which the ketone obtained is subjected successively to a Baeyer-Villiger oxidation and an oxidation of the alcohol obtained (reaction step e). Finally the hydrindanone obtained is subjected to a stereoselective chain-extending reaction (reaction step f), e.g. by a Wittig reaction, to yield the desired stereochemically pure compound having the above formula IX, wherein $R_2$ is methyl and $R_6$ is hydrogen.

The hydrindane intermediate of the above general formula IV is new. Therefore the present invention also relates to this intermediate, which can be prepared as described hereinbefore.

A preferred hydrindane intermediate as defined above can be represented by the general formula

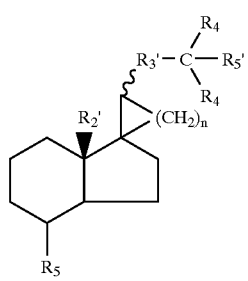

(XVIII)

wherein the symbols have the above meanings.

(C-20)stereochemically pure vitamin D compounds, i.e. vitamin D compounds having a stereochemical purity of at least approx. 90%, can be obtained by using substantially pure hydrindane stereoisomers as intermediates. The present invention therefore also relates to a hydrindane intermediate of the above general formula IV, wherein substituent $R_3$—C$(R_4)_2$—$R_5'$ has either the E or the Z configuration.

The method of preparing these hydrindane stereoisomers is described above.

The hydrindane-4-one intermediate of above general formula V is also new. Therefore the present invention also relates to this intermediate, which can be prepared as described above.

Another new intermediate is the hydrindane intermediate of the above general formula XX. Therefore the present invention also relates to this intermediate, which can be prepared as described above.

To improve the applicability of the new vitamin D compounds of the invention for the above-described pharmacotherapeutic indications, the compounds are usually processed to pharmaceutical compositions, comprising an effective amount of said vitamin D compound as the active ingredient in addition to a pharmaceutically acceptable carrier and/or at least one pharmaceutically acceptable auxiliary substance. Such a composition may be delivered in a dosage unit form for oral, topical (dermal) or parenteral administration, comprising approx. 0.1 μg to approx. 0.1 mg active ingredient per dosage unit.

A composition for diagnostic purposes may comprise, in addition to the vitamin D compound of the present invention, a compatible, non-toxic carrier and/or at least one auxiliary substance.

A cosmetical composition may comprise, in addition to an effective amount (in the range of approx. 0.1 μg to approx. 0.1 mg per dosage unit in a dosage unit form) of the vitamin D compound of the present invention, a cosmetically acceptable, non-toxic carrier and/or at least one auxiliary substance.

Finally the invention relates to a method for the treatment and prophylaxis of a number of disease states including autoimmune diseases (including diabetes mellitus), acne, alopecia, skin aging (including photo-aging), imbalance in the immune system, inflammatory diseases such as rheumatoid arthritis and asthma, as well as diseases related to abnormal cell differentiation and/or proliferation, in a warm-blooded living being, comprising administering to said being or treating said being with a pharmaceutical composition as defined above in a quantity effective for the intended purpose. Examples of such diseases are psoriasis and other hyperproliferative skin diseases.

The present invention also relates to the use of the above pharmaceutical compositions for the treatment of solid, skin and blood cancers, in particular of blood cancers such as leukaemia, of breast cancer, and of skin cancers such as melanoma and squamous cell carcinoma.

The above-defined cosmetical compositions, in particular selected from the group consisting of creams, lotions, ointments, liposomes and gels, can be used for the treatment and prevention of a number of skin disorders, such as inadequate skin firmness or texture, insufficient skin hydration, wrinkles and insufficient sebum secretion.

BRIEF DESCRIPTION OF THE DRAWINGS

Reaction scheme A illustrates a reaction scheme for preparing compound 8 starting from compound 1 as described in Example I and to prepare compound 10 staring from compound 8 as described in Example II or, alternatively, preparing compound 14 starting from compound 8 as described in Example IV and preparing compound 12 starting from compound 10 as described in Example III;

Reaction scheme B illustrates a reaction scheme to prepare compound 21 starting from compound 8 as described in Example V or to prepare compound 28 starting from compound 10 as described in Example VI;

Figure 1:
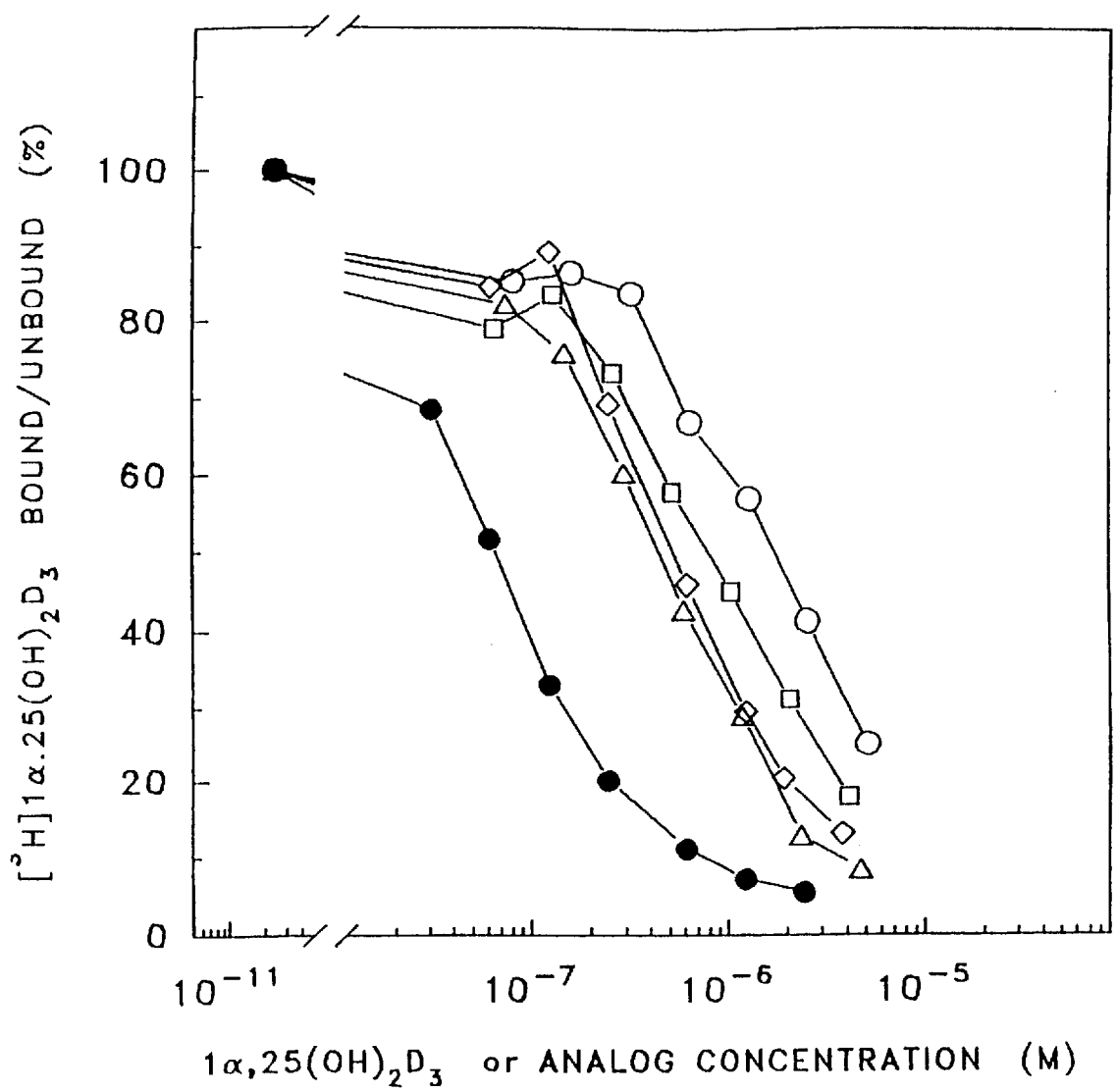
Figure 2:
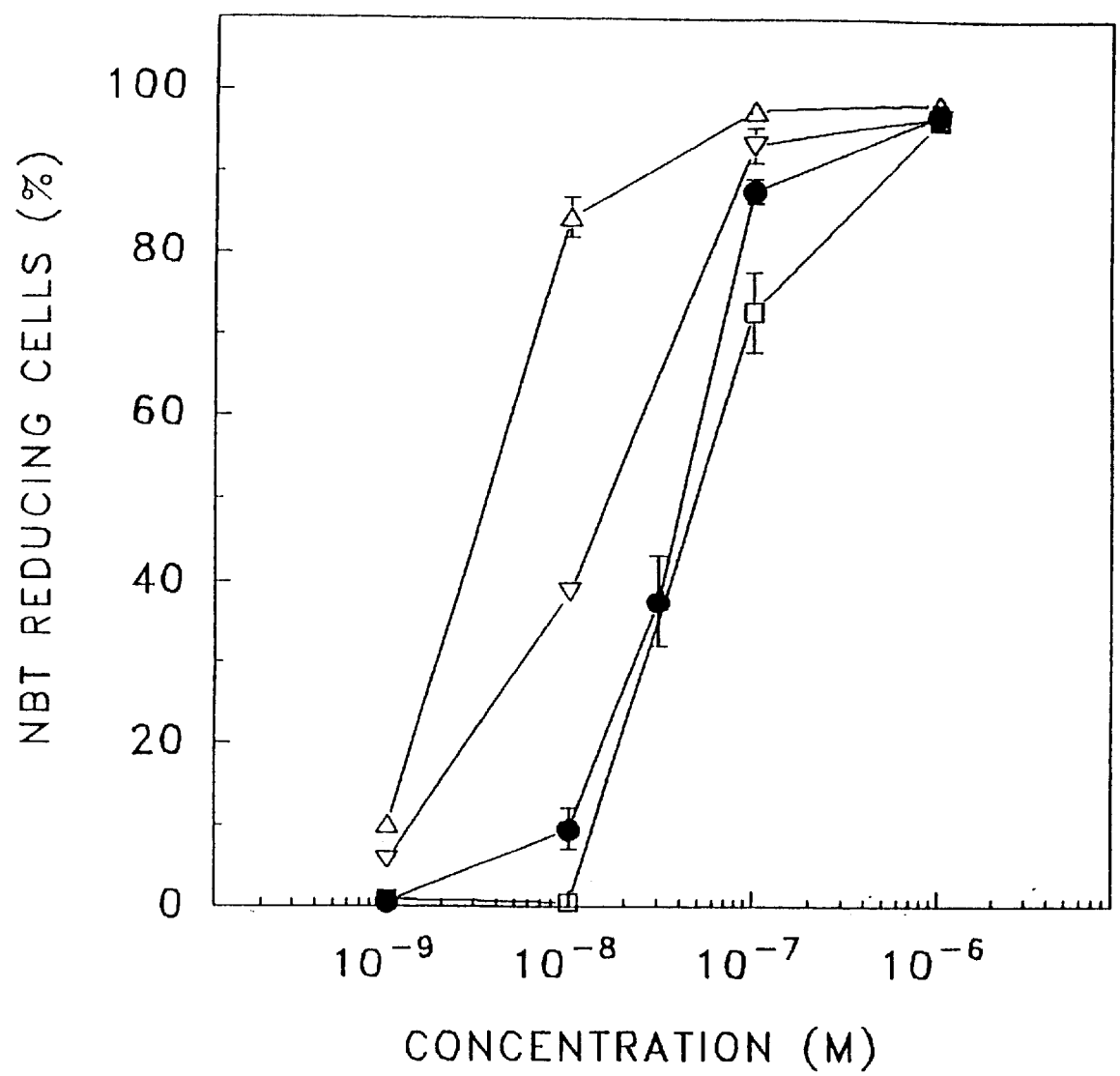
Figure 3:
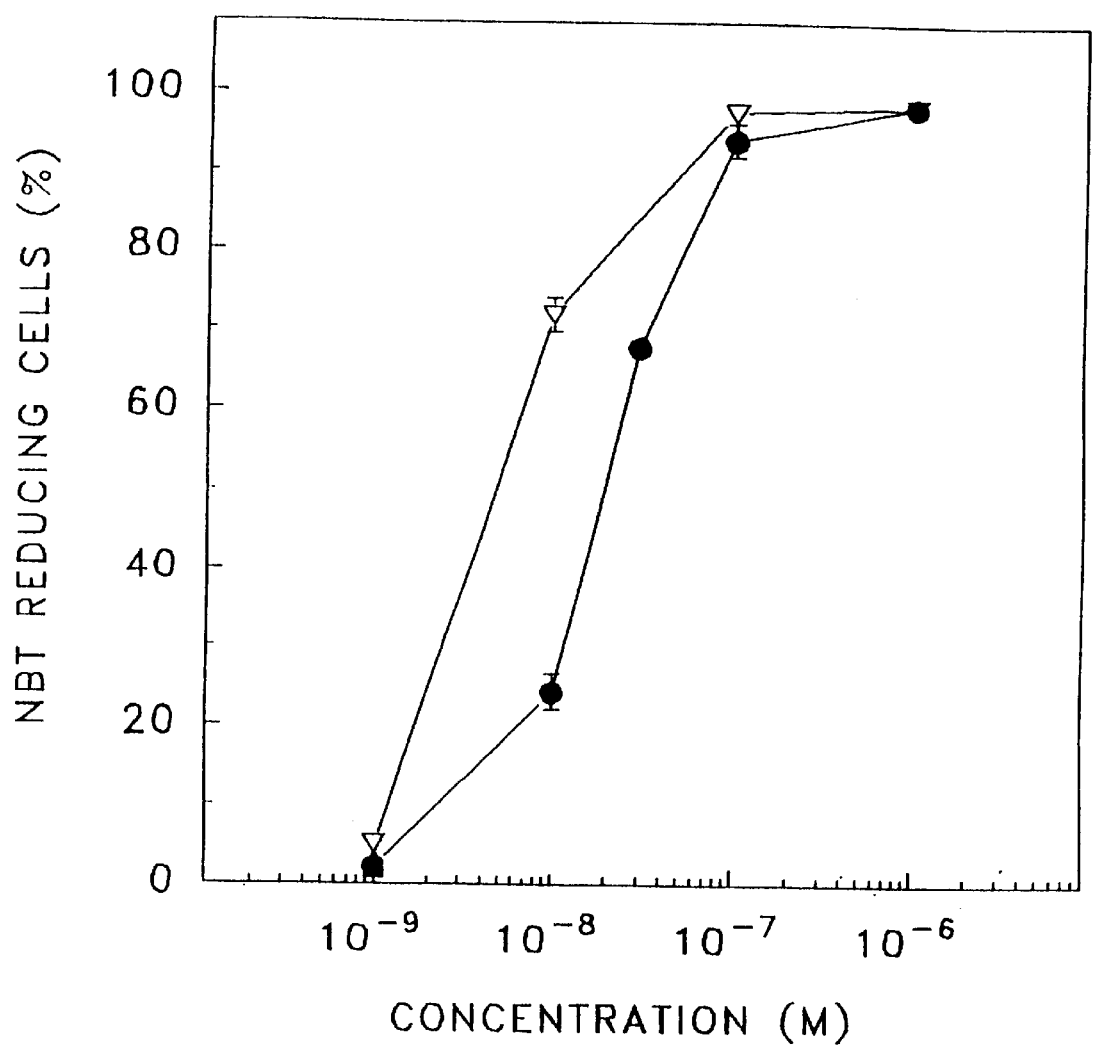

Reaction scheme C in which compound 32 is prepared from starting compound 12 as described in Example VII or, alternatively, compound 36 is prepared starting from compound 14 as described in Example VIII is also illustrated;

FIG. 1 shows the binding of Vitamin D compounds to human Vitamin D binding protein as compared to a known compound; and FIG. 2 and 3 are graphical representations of the differentiating effect of the tested vitamin D compounds on human leukemia cells of the HL-60 line.

The invention will now be described in greater detail with reference to the following specific Examples.

EXAMPLES

Example I

Preparation of compound 8, starting from compound 1. Reaction equation: see Reaction Scheme A attached.

Compound 1 is prepared according to the procedure described by Sestelo, PhD thesis, Santiago de Compostela 1994, 138 or by Dauben et al., Tetrahedron Lett. 1989, 30, 677.

(a). Oxygen is purged through a solution of t-BuOK (1.8 g) in dry t-BuOH (35 ml) at ambient temperature during 10 minutes. A solution of 1 (1.06 g) in dry t-BuOH (20 ml) is added and oxygen is purged through the obtained solution during 10 minutes and nitrogen during 15 minutes. Water (25 ml) is added. The mixture is extracted with $Et_2O$ (3×50 ml). The combined organic phase is dried, filtered and concentrated. The residue is purified by flash chromatography (1–2% EtOAc/hexane) to give 818 mg 2.

(b). To a solution of 2 (110 mg) in $CH_2Cl_2$ (3 ml), cooled down to 0° C., pure m-chloroperbenzoid acid (130 mg) is added. The mixture is stirred at room temperature during 7 days. During these 7 days additional m-chloroperbenzoic acid is added (60 mg after 24 hours, 50 mg after 78 hours, 30 mg after 98 hours and 55 mg after 120 hours). A saturated solution of $NaHCO_3$ (10 ml) and $CH_2Cl_2$ (10 ml) is added. The water phase is extracted with $CH_2Cl_2$. The combined organic phase is dried, filtered and concentrated and the resulting residue is purified by flash-chromatography (1% EtOAc/hexane) to give 81 mg 3.

(c). A solution of 3 (70 mg) in MeOH (2 ml) and water (0.1 ml) is cooled to about 5° C. and NaOH (200 mg) is added. The resulting mixture is stirred at ambient temperature during 12 hours. A saturated solution of $NH_4Cl$ is added, and the methanol is removed. The residue is extracted with $Et_2O$ (4×15 ml). The combined organic phase is dried, filtered and concentrated, yielding a white solid material. The product is purified by flash chromatography (5% EtOAc/hexane) to give 56 mg of 4.

(d). Pyridinium dichromate (85 mg) is added to a solution of 4 (42 mg) in $CH_2Cl_2$ (8 ml). The resulting suspension is stirred at room temperature during 10 hours and filtered through a small layer of hy-flo. The mixture is concentrated and the residue is purified by flash chromatography (3% EtOAc/hexane) to give 38 mg of 5. The product is identified by $^1$H-NMR.

$^1$H-NMR (δ, $CDCl_3$): 4.15 (1H, m, H-8), 2.42 (1H, m, H-16), 2.04–1.68 (2H, m, H-16 and H-14), 1.10 (3H, s, $C_{18}$—$CH_3$), 0.90 (9H, s, $(CH_3)_3CSi$), 0.05 (6H, s, $(CH_3)_2Si$).

(e). A mixture of the Wittig reagent 4-carboxybutyl triphenyl phosphine bromide (9.96 g) and t-BuOK in dry benzene (50 ml) is vigorously stirred at 80° C. during 3 hours. To the suspension a solution of the ketone 5 (1.1 g) in dry benzene is added and the mixture is stirred at 80° C. during 36 hours. The reaction is quenched by adding water (20 ml). The organic phase is washed with water (100 ml). The combined water layers are acidified with a 5% solution of HCl (40 ml) and extracted with EtOAc (6×15 ml). The organic phases are combined, dried and filtered. Concentration affords a residue which is purified by flash chromatography (5% EtOH/hexane) to give 1.05 g of 6.

(f). A solution of MeLi in $Et_2O$ (1.5M, 4 ml) is added to a solution of 6 (1.0 g) in dry THF (10 ml), cooled to 0° C. The mixture is stirred at room temperature during 12 hours and water is added. The water layer is extracted with EtOAc (3×10 ml). The resulting organic phase is washed with a saturated NaCl solution (20 ml), dried and concentrated. The residue is dried over $P_2O_5$ and directly used in the following step.

To a solution of the residue of the last step in dry THF (10 ml) at −78° C., a solution of MeLi in $Et_2O$ (1.5M, 5.6 ml) is added. The resulting mixture is stirred during 3 hours at that temperature and warmed to room temperature. A saturated solution of sodium chloride (15 ml) is added. The water phase is extracted with EtOAc (3×10 ml) and the combined organic phases are dried, filtered and concentrated. Purification by flash chromatography (7–10% EtOAc/hexane) yields 836 mg of compound 7.

(g). To a solution of compound 7 (1.4 g) in dry $CH_2Cl_2$ (30 ml) at 0° C. successively is added i-$Pr_2NEt$ (1.9 ml), dimethylamino pyridine (0.12 g) and methoxymethyl chloride (0.8 ml). The resulting mixture is stirred at room temperature during 21 hours. The reaction is stopped by adding a 5% HCl solution in water (15 ml). The organic phase is washed with water, dried, filtered and concentrated. The residue is purified by flash chromatography (4% EtOAc/hexane), yielding 1.431 g of 8. The product is identified by $^1$H-NMR.

$^1$H-NMR (δ, $CDCl_3$): 4.92 (1H, tt, J=7.4 Hz and 2.0 Hz, H-20), 4.67 (2H, s, $OCOH_2O$), 4.05 (1H, m, H-8), 3.34 (3H, s, $CH_3O$), 2.39 (1H, m, H-16), 2.16 (4H, m, H-22, H-16 and H-14), 1.18 (6H, s, $C_{26,27}$—$CH_3$), 1.08 (3H, s, $C_{18}$—$CH_3$), 0.87 (9H, s, $(CH_3)_3CSi$), −0.01 (6H, 2s, $(CH_3)_2Si$).

Example II

Preparation of compound 10, starting from compound 8. Reaction equation: see Reaction Scheme A attached.

(a). To a solution of 8 (300 mg) in dry $CH_2Cl_2$, $NaHCO_3$ (96 mg, dried under vacuo at 150° C.) and m-chloroperbenzoic acid (150 mg) is added in portions. The resulting suspension is shielded from light and stirred at room temperature during 10 hours. After addition of another portion of m-chloroperbenzoic acid (50 mg), the mixture is stirred for 4 hours. 15 ml of water is added and the water phase is extracted with $CH_2Cl_2$ (3×10 ml). The combined organic phases are dried, filtered and concentrated. The residue is purified by flash chromatography (6% EtOAc/hexane), yielding 285 mg of the epoxide 9.

(b). To a solution of $Ph_2PH$ (0.45 ml) in dry THF (9 ml), cooled to 0° C. and isolated from daylight, a solution of n-BuLi in hexane (2.45M, 1.0 ml) is added. The intense red coloured solution is stirred at room temperature during 4 hours. With the aid of a syringe, a solution of 9 (460 mg) in dry THF (4 ml) is added, and the resulting mixture is stirred during 2 hours. On addition of MeI (0.3 ml) a white suspension results, which is stirred during 3 hours. After addition of water (30 ml), the water phase is extracted with $Et_2O$ (3×15 ml). The combined organic phases are dried, filtered and concentrated. The resulting residue is purified by flash chromatography (5% EtOAc/hexane), yielding 416 mg of 10. The product is identified by $^1$H-NMR.

$^1$H-NMR (δ, $CDCl_3$): 4.90 (1H, tt, J=7.1 Hz and 2.5 Hz, H-20), 4.69 (2H, s, $OCH_2O$), 4.08 (1H, d, J=2.4 Hz, H-8), 2.22 (1H, m, H-16), 3.35 (3H, s, $CH_3O$), 1.20 (6H, s, $C_{26,27}$—$CH_3$), 0.98 (3H, s, $C_{18}$—$CH_3$), 0.89 (9H, s, $(CH_3)_3CSi$), 0.02, 0.01 (6H, 2s, $(CH_3)_2Si$).

Example III

Preparation of compound 12 starting from compound 10. Reaction equation: see Reaction Scheme A attached.

(a). To a solution of 10 (145 mg) in CHCl$_3$ (2 ml), powdered NaOH (205 mg) and Bu$_4$NHSO$_4$ (10 mg) are added. The resulting suspension is stirred at 55° C. during 1 hour. The mixture is cooled to room temperature and diluted with CH$_2$Cl$_2$ (15 ml) and water (20 ml). The water phase is extracted with CH$_2$Cl$_2$ (3×15 ml). The combined organic phase is washed with a saturated solution of NaCl in water (20 ml), dried, filtered and concentrated. The resulting residue is purified by flash chromatography (hexane—2% EtOAc/hexane), yielding 106 mg of compound 11.

(b). To a refluxing solution of 11 (56 mg) in dry THF (1 ml) and dry t-BuOH (0.1 ml), sodium is added in portions. The reaction is continued until the disappearance of solid particles. The reaction mixture is cooled, and ice is added. The mixture is concentrated and water (10 ml) is added followed by extraction with EtOAc (3×10 ml). The combined organic phase is dried, filtered and concentrated. The resulting residue is purified by flash chromatography (2% EtOAc/hexane), yielding 40 mg of 12. The product is identified by $^1$H-NMR.

$^1$H-NMR (δ, CDCl$_3$): 4.71 (2H, s, OC$_2$O), 4.04 (1H, m, H-8), 3.36 (3H, s, CH$_3$O), 2.04–1.94 (1H, m, H-14), 1.22 (6H, S, C$_{26,27}$—CH$_3$), 0.95 (3H, s, C$_{18}$—CH$_3$), 0.89 (9H, s, (CH$_3$)$_3$CSi), 0.76 (1H, dd, J=9.0 Hz and 4.1 Hz, H-21), 0.53–0.41 (1H, m, H-20), −0.14 (1H, dd, J=4.2 Hz and 1.3 Hz, H-21), 0.01 (6H, 2s, (CH$_3$)$_2$Si).

Example IV

Preparation of compound 14, starting from compound 8.
Reaction equation: see Reaction Scheme A attached.

(a). To a solution of 8 (90 mg) in CHCl$_3$ (1.2 ml), powdered NaOH (126 mg) and Bu$_4$NHSO$_4$ (6 mg) is added. The resulting suspension is stirred at 55° C. during 1 hour. The mixture is cooled to room temperature and diluted with CH$_2$Cl$_2$ (10 ml) and water (15 ml). The water phase is extracted with CH$_2$Cl$_2$ (3×10 ml). The combined organic phase is washed with a saturated solution of NaCl in water (20 ml), dried, filtered and concentrated. The resulting residue is purified by flash chromatography (hexane—2% EtOAc/hexane), yielding 88 mg of compound 13.

(b) To a refluxing solution of 13 (230 mg) in EtOH (5 ml), sodium is added in portions. The reaction is continued until the disappearance of solid particles. The reaction mixture is cooled and ice is added. The mixture is concentrated and water (20 ml) is added. Extraction with EtOAc (3×20 ml) yields an organic phase that is dried, filtered and concentrated. The resulting residue is purified by flash chromatography (2% EtOAc/hexane), yielding 180 mg of 14. The product is identified by $^1$H-NMR.

$^1$H-NMR (δ, CDCl$_3$): 4.70 (2H, s, OCH$_2$O), 4.03 (1H, m, H-8), 3.36 (3H, s, CH$_3$O), 2.02–1.92 (1H, m, H-14), 1.21 (6H, s, C$_{26,27}$—CH$_3$), 1.11 (3H, s, C$_{18}$—CH$_3$), 0.89 (9H, s, (CH$_3$)$_3$CSi), 0.69–0.64 (1H, m, H-20), 0.33 (1H, dd, J=5.6 Hz and 4.0 Hz, H-21), 0.17 (1H, dd, J=8.4 Hz and 4.0 Hz, H-21), 0.01 (6H, 2s, (CH$_3$)$_2$Si).

Example V

Preparation of compound 21 starting from compound 8.
Reaction equation: see Reaction Scheme B attached.

(a). To compound 8 (320 mg) a solution of tetrabutyl ammonium bromide (TBAF) in THF (1.1M, 7.5 ml) is added. The resulting mixture is stirred at 60° C. during 22 hours. A cold saturated solution of NaHCO$_3$ (15 ml) and Et$_2$O are added. The water phase is extracted with Et$_2$O (3×10 ml). The combined organic phases are dried, filtered and concentrated. The obtained residue is purified by flash chromatography (15% EtOAc/hexane) to give 233 mg of 15.

(b). To a solution of 15 (221 mg) in dry CH$_2$Cl$_2$ (9.5 ml) pyridinium dichromate (814 mg) is added. The resulting suspension is stirred at ambient temperature during 5 hours. The mixture is filtered through a small layer of silica gel. The silica gel is washed with Et$_2$O and the obtained solution is concentrated. The residue is purified by flash chromatography (15% EtOAc/hexane) to give 208 mg 16. The product is identified by $^1$H-NMR.

$^1$H-NMR (δ, CDCl$_3$): 5.11 (1H, tt, J=7.4 Hz and 2.0 Hz, H-20), 4.71 (2H, s, OCH$_2$O), 3.37 (3H, s, CH$_3$O), 2.59 (1H, dd, J=12.0 Hz and 6.2 Hz, H-14), 2.46 (1H, M, H-16), 2.34–2.24 (2H, m, H-9), 2.20–1.98 (2H, m, H-22), 1.22 (6H, s, C$_{26,27}$—CH$_3$), 0.85 (3H, s, C$_{18}$—CH$_3$).

(c). Lithium diisopropyl amide (LDA) is prepared from dry i-Pr$_2$NH (0.105 ml) and n-BuLi in hexane (2.46M, 0.28 ml) at −78° C. The product is dissolved in dry THF (0.9 ml) and stirred at −78° C. during 10 minutes and at 0° C. during 30 minutes. The solution of LDA is cooled again to −85° C. and slowly added by means of a syringe to a solution of 16 (188 mg) in dry THF (4 ml). The reaction mixture is stirred at −85° C. during 1 hour and at 0° C. during 30 minutes. N-phenyl triflimide (240 mg, recrystallised from hexane) is added and the mixture is stirred at 0° C. during 10 hours. The residue is purified by flash-chromatography (6–10% EtOAc/hexane) to give 175 mg 17.

(d). To a solution of 17 (130 mg) and the enyne 37 (124 mg) in dry DMF (1.6 ml), Et$_3$N (0.14 ml) and (PPh$_3$)$_2$PdCl$_2$ (7 mg) is added. The mixture is heated to 75–80° C. and held at that temperature during 2 hours, during which time the color changes from yellow to black. The reaction mixture is slowly cooled down to room temperature and water is added. The mixture is extracted with Et$_2$O/hexane (1:1, 3×10 ml). The combined organic phase is washed with water (15 ml), dried, filtered and concentrated. The resulting residue is purified by flash chromatography, yielding 138 mg of 18.

(e). To a solution of 18 (91 mg) in hexane (9 ml), a solution of quinoline in hexane (0.4M, 0.19 ml) and Lindlar catalyst (68 mg, dried under vacuo) is added. The solution is isolated from light and purged with H$_2$. The mixture is stirred in a hydrogen atmosphere during 1 hour. Filtration and concentration yields a pale yellow residue of 95 mg of 19, which is used immediately in the following reaction step.

(f). A solution of 19, the product of the previous step, in dry iso-octane (4 ml) is heated to reflux during 4 hours. The mixture is cooled down slowly to ambient temperature and concentrated. The product is purified by flash chromatography (2% Et$_2$O/hexane), yielding 87 mg of 20.

(g). To a solution of 20 (51 mg) in dry EtOH (6 ml) that is deoxygenated with argon, cation exchange resin AG 50W-X4 (1.6 g, washed with EtOH (4×20 ml), dried under vacuo) is added. The resulting suspension, shielded from light, is stirred at ambient temperature during 2 hours. The solid phase is filtered from the solution and washed with EtOAc (4×10 ml). After concentration of the solution a yellow residue is obtained, which is purified by flash chromatography (30–50% EtOAc/hexane), yielding 22 mg of 21. The product is identified by $^1$H-NMR and $^{13}$C-NMR.

$^1$H-NMR (δ, CDCl$_3$): 6.36, 6.04 (2H, AB, d, J=11.1 Hz, H-6 and H-7), 5.33 (1H, s, H-19E), 5.07 (1H, tt, J=7.0 Hz and 1.7 Hz, H-20), 5.00 (1H, s, H-19Z), 4.44 (1H, dd, J=7.1 Hz and 4.7 Hz, H-1), 4.23 (1H, m, H-3), 2.81 (1H, m, H-14), 2.60 (1H, m, H-4), 1.21 (6H, C$_{26,27}$—CH$_3$), 0.75 (3H, s, C$_{18}$—CH$_3$).

$^{13}$C-NMR (δ, CDCl3): 149.5 (C), 147.7 (C), 142.5 (C), 133.3 (C), 124.9 (CH), 120.7 (CH), 117.4 (CH), 111.9 (CH$_2$), 71.1 (C), 70.8 (CH), 66.8 (CH), 56.4 (CH), 47.0 (C), 45.2 (CH$_2$), 43.6 (CH$_2$), 42.8 (CH$_2$), 37.7 (CH$_2$), 31.2 (CH$_2$), 29.2 (CH$_3$), 28.9 (CH$_2$), 28.1 (CH$_2$), 25.4 (CH$_2$), 23.6 (CH$_2$), 23.0 (CH$_2$), 22.6 (CH$_2$), 17.5 (CH$_3$).

Example VI

Preparation of compound 28 starting from compound 10. Reaction equation: see Reaction Scheme B attached.

Compound 28 is prepared from coound 10 via a corresponding reaction sequence as described in Example V. The intermediate hydrindane-4-one 23 is identified by $^1$H-NMR.

$^1$H-NMR (δ, CDCl$_3$): 5.08 (1H, tt, J=7.1 Hz and 2.3 Hz, H-20), 4.69 (2H, s, OCH$_2$O), 3.35 (3H, s, CH$_3$O), 2.43 (1H, dd, J=11.7 Hz and 6.5 Hz, H-14), 2.34–2.19 (3H, m, H-9 and H-16), 1.20 (6H, s, C$_{26,27}$—C$_3$), 0.73 (3H, s, C$_{18}$—CH$_3$).

The final product 28 is identified by $^1$H-NMR and $^{13}$C-NMR.

$^1$H-NMR (δ, CDCl$_3$): 6.38, 6.05 (2H, AB, d, J=11.4 Hz, H-6 and H-7), 5.34 (1H, t, J=1.7 Hz, H-19E), 5.01 (2H, m, H-20 and H-19Z), 4.47 (1H, m, H-1), 4.24 (1H, m, H-3), 2.87–2.82 (1H, m, H-14), 2.64–2.57 (1H, m, H-4), 1.21 (6H, C$_{26,27}$—CH$_3$), 0.63 (3H, s, C$_{18}$—CH$_3$).

$^{13}$C-NMR (δ, CDCl$_3$): 151.8 (C), 147.7 (C), 142.8 (C), 133.2 (C), 124.9 (CH), 117.3 (CH), 116.9 (CH), 111.8 (CH$_2$), 71.1 (C), 70.8 (CH), 66.8 (CH), 54.8 (CH), 46.6 (C), 45.2 (CH$_2$), 43.5 (CH$_2$), 42.8 (CH$_2$), 36.6 (CH$_2$), 29.2 (CH$_3$), 28.9 (CH$_2$), 26.0 (CH$_2$), 24.5 (CH$_2$), 23.4 (CH$_2$), 22.7 (CH$_2$), 19.1 (CH$_3$).

Example VII

Preparation of compound 32 starting from compound 12. Reaction equation: see Reaction Scheme C attached.

Compound 32 is prepared starting from compound 12. Until the intermediate hydrindane-4-one 30 the reaction sequence is corresponding with that described in Example V (first two reaction steps). The intermediate hydrindane-4-one 30 is identified by $^1$H-NMR.

$^1$H-NMR (δ, CDCl$_3$): 4.70 (2H, s, OCH$_2$O), 3.36 (3H, s, CH$_3$O), 2.68 (1H, dd, J=11.0 Hz and 7.4 Hz, H-14), 2.33–2.14 (2H, m, H-9), 1.21 (6H, s, C$_{26,27}$—CH$_3$), 0.93 (1H, dd, J=9.2 Hz and 4.4 Hz, H-21), 0.70 (3H, s, C$_{18}$—CH$_3$), 0.63–0.52 (1H, m, H-20), –0.16 (1H, dd, J=4.9 Hz and 0.5 Hz, H-21). Starting from compound 30 the following reactions are carried out to obtain compound 32.

(a). An amount of 38 (128 mg) is dissolved in THF (4 ml) and cooled down to –78° C. A solution of n-BuLi in hexane (1.92M, 0.115 ml) is added slowly, during which addition an intense red colour is formed. The mixture is stirred for 30 minutes at –85° C., followed by a slow addition of a solution of 30 (53 mg) in dry THF (1 ml). The reaction mixture is stirred at –70° C. during 90 minutes, at –30° C. during 1 hour and at ambient temperature during 2 hours. The reaction is quenched by addition of a drop of water. After concentration, water is added and the resulting mixture is extracted with EtOAc (2×15 ml). The combined organic phase is washed with a saturated solution of NaCl in water (15 ml), dried, filtered and concentrated. The resulting residue is purified by flash-chromatography to give 109 mg of 31.

(b). To a solution of 31 (40 mg) in dry MeOH (6 ml), deoxygenated with argon, cation exchange resin AG 50W-X4 (1.7 g, washed with MeOH (4×20 ml), dried in vacuo) is added. The resulting suspension is shielded from light, stirred at ambient temperature during 2 days and filtered. The solid material is washed with EtOAc (4×10 ml). After concentration of the solution a yellow residue is obtained, which is purified by flash chromatography (30–50% EtOAc/hexane) to give 19 mg of 32. The product is identified by $^1$H-NMR and $^{13}$C-NMR.

$^1$H-NMR (δ, CDCl$_3$): 6.36, 6.05 (2H, AB, d, J=11.2 Hz, H-6 and H-7), 5.30 (1H, H-19E), 4.97 (2H, s, H-20 and H-19Z), 4.37 (1H, dd, J=7.0 Hz and 4.6 Hz, H-1), 4.16 (1H, m, H-3), 2.83 (1H, dd, J=12.0 Hz and 3.6 Hz, H-14), 2.55 (1H, dd, J=13.3 Hz and 3.5 Hz, H-4), 2.30–2.20 (2H, m, H-9), 1.17 (6H, C$_{26,27}$—CH$_3$), 0.59 (3H, s, C$_{18}$—CH$_3$), 0.55–0.47 (1H, m, H-20), –0.19 (1H, dd, J=4.6 Hz and 0.8 Hz, H-21).

$^{13}$C-NMR (δ, CDCl$_3$): 148.6 (C), 143.6 (C), 134.1 (C), 125.1 (CH), 117.4 (CH), 111.9 (CH$_2$), 71.2 (CH), 67.2 (CH), 55.3 (CH), 45.8 (CH$_2$), 44.6 (CH$_2$), 44.3 (C), 43.4 (CH$_2$), 37.0 (C), 36.3 (C), 34.6 (CH$_2$), 32.1 (CH$_2$), 30.1 (CH), 30.0 (CH$_2$), 29.5 (CH$_3$), 28.7 (CH$_2$), 25.3 (CH$_2$), 23.5 (CH$_2$), 18.0 (C), 17.9 (CH), 17.3 (CH$_3$).

Example VIII

Preparation of compound 36 starting from compound 14. Reaction equation: see Reaction Scheme C attached.

Compound 36 is prepared from compound 14 via a corresponding reaction sequence as described in Example VII. The intermediate hydrindane-4-one 34 is identified by $^1$H-NMR.

$^1$H-NMR (δ, CDCl$_3$): 4.70 (2H, s, OCH$_2$O), 3.36 (3H, s, CH$_3$O), 2.71 (1H, dd, J=11.6 Hz and 7.7 Hz, H-14), 2.31–2.15 (2H, m, H-9), 1.21 (6H, s, C$_{26,27}$—CH$_3$), 0.83 (3H, s, C$_{18}$—CH$_3$), 0.84–0.71 (1H, m, H-20), 0.50 (1H, dd, J=5.7 Hz and 4.2 Hz, H-21), 0.36 (1H, dd, J=8.6 Hz and 4.2 Hz, H-21).

The final product 36 is identified by $^1$H-NMR and $^{13}$C-NMR.

1H-NMR (δ, CDCl$_3$): 6.36, 6.05 (2H, AB, d, J=11.3 Hz, H-6 and H-7), 5.30 (1H, H-19E), 4.97 (2H, dd, J=2.1 Hz and 1.2 Hz, H-20 and H-19Z), 4.37 (1H, dd, J=7.2 Hz and 4.5 Hz, H-1), 4.16 (1H, m, H-3), 2.86–2.79 (1H, m, H-14), 2.55 (1H, dd, J=13.3 Hz and 3.4 Hz, H-4), 2.30–2.22 (2H, m, H-9), 1.16 (6H, C$_{26,27}$—CH$_3$), 0.74 (3H, s, C$_{18}$—CH$_3$), 0.77–0.64 (1H, m, H-20), 0.46 (1H, dd, J=5.7 Hz and 4.1 Hz, H-21), 0.28 (1H, dd, J=8.6 Hz and 4.0 Hz, H-21).

$^{13}$C-NMR (δ, CDCl$_3$): 148.6 (C), 143.3 (C), 134.1 (C), 125.0 (CH), 117.8 (CH), 111.9 (CH$_2$), 71.1 (CH), 67.2 (CH), 60.6 (C), 56.5 (CH), 45.7 (CH$_2$), 44.8 (C), 44.3 (CH$_2$), 43.4 (CH$_2$), 38.1 (CH$_2$), 37.0 (C), 36.1 (CH$_2$), 30.5 (CH$_2$), 30.1 (CH$_2$), 29.4 (CH$_3$), 25.7 (CH$_2$), 25.0 (CH$_2$), 23.7 (CH$_2$), 23.7 (CH), 19.1 (CH$_2$), 16.5 (CH$_3$).

Example IX

Affinity to intracellular vitamin D receptor.

Vitamin D compounds according to the invention are dissolved in ethanol in concentrations ranging from $10^{-13}$ to $10^{-7}$M. The affinity towards the calf thymus intracellular vitamin D receptor (VDR) is determined in a biological assay. In this assay, $^3$H-1α,25-dihydroxycholecalciferol ($^3$H-1α,25-DHCC), which is specifically bound to the VDR, is replaced by the tested compounds. The tested compound 32 has a high VDR-affinity, comparable to that of 1α,25-dihydroxycholecalciferol. A high VDR-affinity is indicative for a biologically active substance. The tested compounds 21 and 28 have moderate VDR-affinities, whereas tested compound 36 has a weak VDR-affinity.

Example X

Affinity to vitamin D binding protein.

Vitamin D binding protein (DBP) is the specific carrier for vitamin D and its metabolites in blood. The biological activity of vitamin D compounds depends on their binding to DBP, because strong binding to DBP will reduce the intracellular access to the VDR. Binding to the DBP may also influence the half-life of the vitamin D derivatives in circulation. Weak binders are rapidly metabolized, which is a favourable aspect in topical application.

In the assay, DBP is incubated with $^3$H-1α,25-DHCC and 1α,25-DHCC or with several vitamin D compounds according to the invention. To this purpose, the vitamin compounds are dissolved in ethanol in concentrations ranging from $10^{-11}$ to $2.5 \times 10^{-6}$M. The percentage bound/unbound $^3$H-1α, 25-DHCC is then calculated. DBP is purified from total human serum. The results are shown in the appended FIG. 1. FIG. 1 shows the binding of vitamin D compounds to human vitamin D binding protein. [$^3$H]1α,25(OH)$_2$D$_3$=$^3$H-1α,25-DHCC; in the Figure •=1α,25-DHCC (known compound); □=compound 21; Δ=compound 28; o=compound 32 and ◇=compound 36.

Tested Compounds 21, 28, 32 and 36 all bind rather weakly to the DBP, compared to the known compound 1α,25-DHCC.

Example XI

Cell differentiation.

Vitamin D compounds according to the invention are dissolved in ethanol in concentrations ranging from $10^{-12}$ to $10^{-6}$M and tested for their capacity to induce cell differentiation in a HL-60 assay. In this assay, biochemical examination of the human leukemic cell line HL-60 is done, in order to establish whether cell differentiation has taken place.

Differentiation is expressed as the maturation parameter nitroblue tetrazolium (NBT) reduction. After culturing with the known 1α,25-DHCC or with vitamin D compounds of the invention, the percentage of cells containing black formazan deposits is determined. An increase in the percentage of NBT reducing cells indicates an increase in cell differentiation.

The vitality and proliferation of the cells in the HL-60 cultures are good in all conditions tested. 1α,25-DHCC (known), compound 21, compound 28, compound 32 and compound 36 all induce differentiation and maturation of the HL-60 cells. The optimum effect is found at concentrations in the range of $10^{-8}$ to $10^{-7}$M.

The NBT-reduction inducing capacity of compound 36 is about 10× stronger than that of the known 1α,25-DHCC. Compound 21 and 32 are 3–5 times more potent in inducing NBT-reduction than 1α,25-DHCC (FIGS. 2 and 3). Compound 28 is as potent as the known 1α,25-DHCC.

The above implies that the tested new vitamin D compounds of the invention display a higher than or at least the same cell differentiating activity as the known 1α,25-DHCC.

FIGS. 2 and 3 (appended) show the differentiating effect of the tested vitamin D compounds on human leukemia cells of the HL-60 line. In both Figures •=1α,25-DHCC; in FIG. 2 ▽ is compound 21 and □ is compound 28; and Δ=compound 36; in FIG. 3, ▽=compound 32.

We claim:

1. A vitamin D compound of the general formula

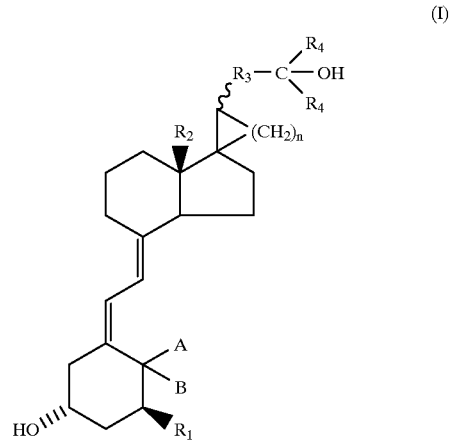

(I)

wherein:

R$_1$ is a hydrogen atom or a hydroxy group;

R$_2$ is a (C$_1$–C$_3$)alkyl group, a hydro(C$_1$–C$_3$)alkyl group, a (C$_1$–C$_2$)alkoxymethyl group or a (C$_2$–C$_3$)alkenyl or alkynyl group;

n is 1;

R$_3$ is a branched or non-branched, saturated or unsaturated aliphatic (C$_3$–C$_7$) hydrocarbon or oxahydrocarbon biradical, having at least 3 atoms in the main chain and being optionally substituted with one or more substituents selected from fluoro, hydroxy, epoxy or methoxy;

R$_4$ is a branched or straight (C$_1$–C$_6$)alkyl group or a (C$_3$–C$_6$)cycloalkyl group; and A and B are each individually hydrogen atoms or methyl groups, or A and B form together a methylene group.

2. A vitamin D compound as claimed in claim 1, having the general formula

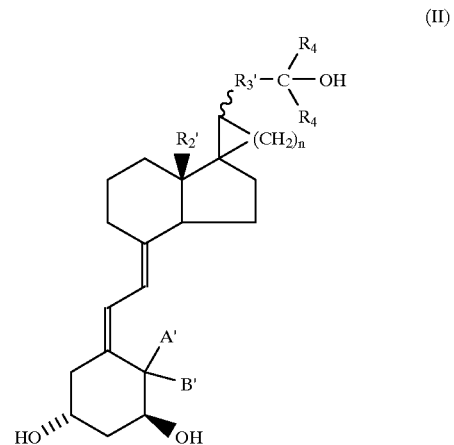

(II)

wherein:

R$_4$ and n have the meanings given in claim 1;

R$_2$' is CH$_3$, CH$_2$CH$_3$, CH$_2$OH or CH=CH$_2$;

R$_3$' is a biradical of the formula —CH$_2$—CH$_2$—(CH$_2$)$_m$—, —CH$_2$—(CH$_2$)$_m$—CH(CH$_3$)— or —(CH$_2$)$_p$—O—(CH$_2$)$_q$—, wherein m=1–3, p=0–3 and q=0–3 with the proviso that p+q≧2; and A' and B' are hydrogen atoms or form together a methylene group.

3. A vitamin D compound as claimed in claim 2, having the general formula

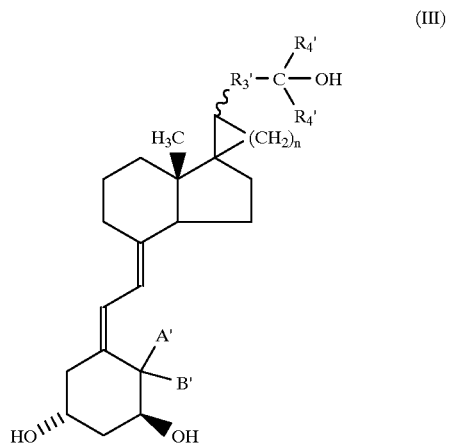

(III)

wherein:
n is 1;
$R_3'$, A' and B' have the meanings given in claim 2; and
$R_4'$ is methyl, ethyl, propyl, isopropyl or cyclopropyl.

4. A vitamin D compound as claimed in any one of the preceding claims, wherein the (C-20) substituent, i.e. substituent $R_3$—$C(R_4)_2$—OH, is the E configuration.

5. A pharmaceutical composition comprising, in addition to a pharmaceutically acceptable carrier and/or at least one pharmaceutically acceptable auxiliary substance, as the active ingredient at least one compound as defined in claim 1, or 2 or 3 in an effective amount.

6. A vitamin D compound as claimed in any one of claims 1–3, where the (C-20) substituent, i.e. substituent $R_3$—$C(R_4)_2$—OH, is the Z configuration.

7. A pharmaceutical composition comprising an effective amount of at least one compound according to claim 4 and at least one member of the group consisting of a pharmaceutically acceptable carrier and a pharmaceutically acceptable auxiliary substance.

8. A pharmaceutical composition comprising an effective amount of at least one compound according to claim 6 and at least one member of the group consisting of a pharmaceutically acceptable carrier and a pharmaceutically acceptable auxiliary substance.

* * * * *